US008858920B2

(12) United States Patent
Robinson et al.

(10) Patent No.: US 8,858,920 B2
(45) Date of Patent: Oct. 14, 2014

(54) ANTI-CARIES ORAL CARE COMPOSITION WITH XYLITOL

(75) Inventors: Richard S. Robinson, Belle Mead, NJ (US); David P. Muscle, Princeton, NJ (US); Richard J. Sullivan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 964 days.

(21) Appl. No.: 11/020,010

(22) Filed: Dec. 21, 2004

(65) Prior Publication Data

US 2006/0286044 A1 Dec. 21, 2006

(51) Int. Cl.
*A61K 8/00* (2006.01)
*A61K 8/18* (2006.01)
*A61Q 11/00* (2006.01)
*A61K 8/368* (2006.01)
*A61K 8/365* (2006.01)
*A61K 8/34* (2006.01)
*A61K 8/55* (2006.01)

(52) U.S. Cl.
CPC .......... *A61Q 11/00* (2013.01); *A61K 8/368* (2013.01); *A61K 8/365* (2013.01); *A61K 8/345* (2013.01); *A61K 8/55* (2013.01)
USPC .......................................................... 424/49

(58) Field of Classification Search
USPC .......................................................... 424/49
See application file for complete search history.

(56) References Cited

U.S. PATENT DOCUMENTS

| | | | |
|---|---|---|---|
| 4,193,988 A | 3/1980 | Forward et al. | |
| 4,283,385 A | 8/1981 | Dhabhar et al. | |
| 4,431,628 A | 2/1984 | Gaffar | |
| 4,460,565 A | 7/1984 | Weststrate et al. | |
| 4,606,912 A * | 8/1986 | Rudy et al. | 424/52 |
| 4,935,227 A * | 6/1990 | Duckworth | 424/52 |
| 5,079,001 A * | 1/1992 | Affolter | 514/567 |
| 5,089,255 A | 2/1992 | Gaffar et al. | |
| 5,116,602 A | 5/1992 | Robinson et al. | |
| 5,378,131 A | 1/1995 | Greenberg | |
| 5,571,502 A | 11/1996 | Winston et al. | |
| 5,614,175 A | 3/1997 | Winston et al. | |
| 5,776,435 A | 7/1998 | Gaffar et al. | |
| 5,866,102 A | 2/1999 | Winston et al. | |
| 5,891,448 A | 4/1999 | Chow et al. | |
| 5,958,380 A | 9/1999 | Winston et al. | |
| 5,976,507 A | 11/1999 | Wong et al. | |
| 5,993,786 A | 11/1999 | Chow et al. | |
| 6,010,684 A | 1/2000 | Wiedemann | |
| 6,054,119 A | 4/2000 | Hurme et al. | |
| 6,106,812 A * | 8/2000 | Prencipe et al. | 424/53 |
| 6,120,754 A | 9/2000 | Lee et al. | |
| 6,136,298 A | 10/2000 | Gaffar et al. | |
| 6,143,330 A | 11/2000 | Aaltonen et al. | |
| 6,207,138 B1 | 3/2001 | Zhang et al. | |
| 6,207,139 B1 | 3/2001 | Lee et al. | |
| 6,214,320 B1 | 4/2001 | Gaffar et al. | |
| 6,214,321 B1 | 4/2001 | Lee et al. | |
| 6,238,648 B1 | 5/2001 | Leusch et al. | |
| 6,248,310 B1 | 6/2001 | Lee et al. | |
| 6,372,198 B1 * | 4/2002 | Abbate | 424/49 |
| 6,440,394 B2 | 8/2002 | Barth et al. | |
| 6,447,754 B1 | 9/2002 | Kligerman et al. | |
| 2001/0046475 A1 | 11/2001 | Barth et al. | |
| 2003/0206874 A1 | 11/2003 | Doyle et al. | |
| 2003/0220336 A1 * | 11/2003 | Jung | 514/235.5 |
| 2004/0037790 A1 * | 2/2004 | Watanabe | 424/58 |
| 2004/0047814 A1 * | 3/2004 | Xu et al. | 424/49 |
| 2005/0025720 A1 | 2/2005 | Bailey | |

FOREIGN PATENT DOCUMENTS

| | | |
|---|---|---|
| CN | 1208604 | 2/1999 |
| JP | 11 106322 | 4/1999 |
| JP | 2001-348316 A | 12/2001 |
| KR | 2003-0062944 A | 7/2003 |
| RU | 1 806 738 | 4/1993 |
| WO | WO 95/07685 | 3/1995 |
| WO | WO 03/059304 | 7/2003 |
| WO | WO 2004/060336 | 7/2004 |
| WO | WO 2005/004824 | 1/2005 |

OTHER PUBLICATIONS

Science Lab MSDS, Calcium Carbontae, created Oct. 10, 2005, last updated May 21, 2013.*
International Search Report and Written Opinion in International Application No. PCT/US05/042047, mailed Apr. 3, 2006.
International Search Report and Written Opinion in International Application No. PCT/US05/042164, mailed May 31, 2006.
The Cosmetic, Toiletry, and Fragrance Association, Chelating Agents (International Cosmetic Ingredient Handbook, 10th ed., CD-ROM, rel. 2004).

* cited by examiner

*Primary Examiner* — Benjamin Packard
(74) *Attorney, Agent, or Firm* — Howard C. Lee

(57) ABSTRACT

An oral care composition comprises xylitol and a water-soluble calcium salt for caries prevention. Methods of treating and preventing dental caries are also provided.

13 Claims, No Drawings

ANTI-CARIES ORAL CARE COMPOSITION WITH XYLITOL

INTRODUCTION

The present invention relates to oral care compositions, particularly compositions for caries prevention.

Dental caries are caused by the production of acid by certain bacteria, including *Streptococcus mutans* (hereinafter *S. mutans*). *S. mutans* produces sticky, adhesive glucans and fructans from fermentable sugars, particularly sucrose, which promote the adhesion of bacteria to the oral surfaces. The *S. mutans* may be contained in a dental plaque—the soft material formed of a complex mass of bacteria in a polysaccharide matrix which surrounds the teeth. A cariogenic plaque containing a high proportion of *S. mutans* can often contain $2 \times 10^8$ bacteria per mg wet weight and can rapidly convert fermentable sugars (sucrose, glucose, or fructose, for example) to generate enough acid to lower the pH of the plaque to 5.5 or lower.

Demineralization of enamel occurs in an oral environment having a low pH because the natural equilibrium between hydroxyapatite being dissolved from the enamel of teeth and hydroxyapatite being formed on or in the teeth from substances occurring naturally in the saliva is disrupted. While saliva can reduce the acidity of the oral environment and provide a continuing source of calcium and phosphate to the tooth enamel, which tends to remineralize the enamel and inhibit or reverse the carious process, once the acid attack causes sufficient progression of the demineralization, a full-fledged carious lesion develops. For further discussion, see U.S. Pat. No. 6,136,298, Gaffar, et al., issued Oct. 24, 2000; U.S. Pat. No. 5,378,131 Greenberg, issued Jan. 3, 1995; and U.S. Pat. No. 5,089,255, Gaffar, et al. issued Feb. 18, 1992.

Current methods of preventing dental caries include fluoride treatments and other anti-cariogenic oral care compositions used as part of a personal or a professional oral care regimen. Other methods include inhibiting acid production by disrupting metabolism of the *S. mutans* to kill the cells. Nonetheless, caries are still a prevalent dental problem.

Thus, there is an ongoing need to provide anti-cariogenic oral care compositions. It would be desirable to provide an oral care composition that prevents cariogenic conditions and remineralizes demineralized enamel.

SUMMARY

The present invention relates to oral care compositions comprising xylitol and a water-soluble calcium salt, where the xylitol and the calcium salt are present in a weight ratio of at least about 10:1.

The present invention also provides methods of preventing or treating dental caries comprising administering a safe and effective amount of an oral care composition to the oral cavity of a subject, the composition comprising xylitol and a water-soluble calcium salt, where the xylitol and the calcium salt are present in a weight ratio of at least about 10:1.

The present invention also provides oral care compositions comprising xylitol, calcium glycerophosphate and fluoride providing agents in anti-cariogenic amounts, where the xylitol and calcium glycerophosphate are present in a weight ratio of at least about 10:1.

It has been discovered that the compositions and methods of this invention afford advantages over anti-caries compositions known in the art. Such advantages include providing an oral care composition highly effective to remineralize demineralized dental surfaces. Further uses, benefits, and embodiments of the present invention are apparent from the description set forth herein.

DETAILED DESCRIPTION

The following description of the preferred embodiment(s) is merely exemplary in nature and is in no way intended to limit the invention, its application, or uses.

The following definitions and non-limiting guidelines must be considered in reviewing the description of this invention set forth herein. The headings (such as "Introduction" and "Summary") and sub-headings (such as "Compositions" and "Methods") used herein are intended only for general organization of topics within the disclosure of the invention, and are not intended to limit the disclosure of the invention or any aspect thereof. In particular, subject matter disclosed in the "Introduction" may include aspects of technology within the scope of the invention and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being a "system" or "carrier") is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

As referred to herein, all compositional percentages are by weight of the total composition, unless otherwise specified.

"A" and "an" as used herein indicate "at least one" of the item is present. As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

Compositions

The present invention provides oral care compositions and methods for administration or application to, or use with, a human or other animal subject. As referred to herein, an "oral care composition" is any composition that is suitable for administration or application to the oral cavity a human or animal subject for enhancing the health, hygiene or appearance of the subject, preferably providing such benefits as: the prevention or treatment of a condition or disorder of the teeth, gums, mucosa or other hard or soft tissue of the oral cavity; the prevention or treatment of a systemic condition or disorder; the provision of sensory, decorative, or cosmetic benefits; and combinations thereof. In various preferred embodiments, an oral care composition is not intentionally swallowed, but is rather retained in the oral cavity for a time sufficient to effect the intended utility. Preferably, specific materials and compositions to be used in this invention are, accordingly, pharmaceutically-acceptable. As used herein, "safe and effective amount" or a "pharmaceutically acceptable" or "cosmetically acceptable" component refers to a composition that is suitable for use with humans and/or animals to provide the desired therapeutic, prophylactic, sensory, decorative, or cosmetic benefit without undue adverse side effects (such as toxicity, irritation, and allergic response) commensurate with a reasonable benefit/risk ratio when used in the manner of this invention.

The present invention provides oral care compositions comprising xylitol and a water-soluble calcium salt which help remineralize demineralized tooth enamel and prevent the development of dental caries.

Xylitol

Xylitol is a non-cariogenic carbohydrate and has a variety of uses including, but not limited to, a non-cariogenic sweetener, a humectant, and an anti-caries agent. While not intending to be bound by any particular theory, xylitol appears to cause a disturbance in the metabolism of fermentable carbohydrates by *S. mutans* and thereby decreases plaque formation and reduces plaque adhesion to the pellicle. Also, upon metabolizing xylitol, the toxic metabolite xylitol-5-phosphate forms within the *S. mutans* cells which may interfere with glycolysis energy production and may also involve an energy-consuming futile cycle. The energy consuming cycle kills the *S. mutans* which results in reduced caries. Xylitol may be present in the composition as an anti-caries agent at about 5% to about 20% by weight, preferably from about 8% to about 15% by weight.

Water-Soluble Calcium Salt

Water-soluble calcium salts include calcium chloride, calcium acetate, calcium butyrate, calcium citrate, calcium lactate, calcium salicylate, and calcium glycerophosphate. Preferably, the salt is readily dissolvable and stays dissolved in water. A preferred calcium salt is calcium glycerophosphate (CGP). While not intending to be bound by any particular theory, CGP is believed to reduce demineralization and/or increase remineralization of tooth enamel. At low pHs caused by a high concentration of *S. mutans* in the plaque, the addition of calcium and phosphate ions provides a buffer that shifts the hydroxyapatite equilibrium towards remineralization. Further benefits of CGP include the ability to initiate remineralization at pH levels as low as 5 and the ability to bind directly to the enamel surface.

CGP is also known as calcium glycerol phosphate, 1-(dihydrogen phosphate)-1,2-3-propanetriol, calcium salt, 2-(dihydrogen phosphate)-1,2,3-propanetriol, calcium salt (1:1), 1,2,3-propanetriol, 2-(dihydrogen phosphate), calcium salt (1:1), and 1,2,3-propanetriol, mono(dihydrogen phosphate), calcium salt (1:1). CGP may exist as a hydrate, including the monohydrate and the dihydrate. CGP also has the forms α-calcium glycerophosphate or β-calcium glycerophosphate. The α-calcium glycerophosphate, β-calcium glycerophosphate, and mixtures thereof may be employed in embodiments of the invention. An α- and β-CGP mixture may have any α-CGP:β-CGP ratio, for example, 80 parts α-CGP to 20 parts β-CGP. CGP may be purchased from NutriScience Innovations, LLC (Fairfield, Conn., United States) as calcium glycerophosphate NF—X. In various embodiments, it may be desirable to combine CGP and one or more additional calcium salts having solubility properties different from that of CGP. The different solubilities may provide greater control in the amount and ratios of calcium and/or phosphate ions released in the composition as explained in U.S. Pat. No. 6,447,754, Kligerman, et al., issued Sep. 10, 2002.

The water-soluble calcium slat contains at least about 19% by weight calcium ions. Generally, the water-soluble calcium salt releases from about 100 to about 1,000 ppm of calcium ions into the oral care composition, preferably from about 200 to about 500 ppm. The water-soluble calcium salt is present in the composition at about 0.01% to about 1% by weight, preferably from about 0.08% to about 0.3% by weight.

The xylitol and the water-soluble calcium salts are present in the composition in a ratio of at least about 10:1 by weight or a molar ratio of at least about 12:1, respectively. In various embodiments, the xylitol and the water-soluble calcium salts may are present at up to about 200:1 by weight or a molar ratio of up to about 240:1, respectively. Preferred ranges of xylitol to water-soluble calcium salt weight ratios include from about 10:1 to about 200:1, preferably from about 25:1 to about 100:1, and more preferably from about 65:1 to about 80:1, respectively.

The composition may further comprise a fluoride-providing agent or a fluoride-ion source. The fluoride-providing agents are well known as anti-caries agents. The fluoride-providing agents are sufficiently water soluble to release an anti-carious amount of fluoride ions in water or the saliva. Suitable fluoride-providing agents are organic or inorganic.

Inorganic fluoride ion-providing agents include metal, alkali metal, alkaline earth metal and ammonium salts of fluoride, such as for example potassium fluoride, sodium fluoride, ammonium bifluoride, calcium fluoride, a copper fluoride such as cuprous fluoride, barium fluoride, sodium fluorosilicate, ammonium fluorosilicate, sodium fluorozirconate, sodium monofluorophosphate, aluminum mono- and di-fluorophosphate, fluorinated sodium calcium pyrophosphate, stannous fluoride, lithium fluoride, cesium fluoride, aluminum fluoride, cupric fluoride, indium fluoride, stannous fluorozirconate, ferric fluoride, nickel fluoride, palladium fluoride, silver fluoride, zirconium fluoride, and mixtures thereof. Preferred inorganic fluoride ion-providing agents are sodium monofluorophosphate and sodium fluoride.

Organic fluoride ion-providing agents include hexylamine hydrofluoride, laurylamine hydrofluoride, myristylamine hydrofluoride, decanolamine hydrofluoride, octadecenylamine hydrofluoride, myristoxyamine hydrofluoride, diethylaminoethyloctoylamide hydrofluoride, diethanolaminoethyloleylamide hydrofluoride, diethanolaminopropyl-N'-octadecenylamine dihydrofluoride, 1-ethanol-2-hexadecylimidazoline dihydrofluoride, octoylethanolamine hydrofluoride, octyltrimethylammonium fluoride, dodecylethyldimethylammonium fluoride, tetraethylammonium fluoride, dilauryldimethylammonium fluoride, 88-9 octadecenylbenzyldimethylammonium fluoride, dioctyldiethylammonium fluoride, cyclohexylcetyldimethylammonium fluoride, furfuryllauryidimethylammonium fluoride, phenoxyethylcetyldimethylammonium fluoride, N:N'-tetramethyl-N:N'-dilaurylethylenediammonium difluoride, N-cetylpyridinium fluoride, N:N-dilauryl-morpholinium fluoride, N-myristyl-N-ethylmorpholinium fluoride, N-(octylaminocarbonylethyl)-N-benzyldimethylammonium fluoride, N-(B-hydroxydodecyl)trimethylammonium fluoride, N-phenyl-N-hexadecyldiethylammonium fluoride, N-cyclohexyl-N-octadecyldimethylammonium fluoride, N-(2-carbomethoxyethyl)-N-benzyldimethylammonium fluoride, N-(2-carbocyclohexoxyethyl)-N-myristyldimethylammonium fluoride, N-(2-carbobenzyloxyethyl)-N-dodecyldimethylammonium fluoride, N-[2-(N:N'-dimethylaminocarbonyl)-ethyl]-N-dodecyldiethylammonium fluoride, N-carboxymethyl-N-cicosyldimethylammonium fluoride, olaflur (N'-octadecyltrimethylendiamine-N,N,N'-tris(2-ethanol)-dihydrofluoride), betaine hydrofluoride, sarcosine stannous fluoride, alanine stannous fluoride, glycine potassium fluoride, sarcosine potassium fluoride, glycine hydrofluoride, lysine hydrofluoride, alanine hydrofluoride, betaine zirconium fluoride, and mixtures thereof.

The fluoride-providing agent is present in an amount sufficient to release between about 200 ppm to 3000 ppm fluoride ion, preferably from about 800 to about 1500 ppm fluoride ion. The fluoride-providing agent may be present in the composition from about 0.001% to about 3% by weight.

Embodiments of the present invention may also include preservatives such as parabens, including propyl paraben (propyl parahydroxy benzoate) and methyl paraben, dehydroacetic acid, sorbic acid, sodium benzoate, potassium sorbate, and mixtures thereof. These and other suitable preservatives are disclosed U.S. Pat. No. 5,116,602, Robinson, et al., issued May 26, 1991; and U.S. Pat. No. 4,431,628, Gaffar, issued Feb. 14, 1984. A preferred mixture comprises methyl paraben and propyl paraben. The preservative is present in the composition at about 0.001% to about 0.2% by weight, preferably from about 0.07% to about 0.12% by weight.

Orally Acceptable Carrier

As used herein, an "orally acceptable carrier" refers to a material or combination of materials that are safe for use in the compositions of the present invention, commensurate with a reasonable benefit/risk ratio, with which the xylitol and water-soluble calcium salt may be associated while retaining significant efficacy. Preferably, the carrier does not substantially reduce the efficacy of the active materials of the present compositions. Selection of specific carrier components is dependent on the desired product form, including dentifrices, rinses, gels, paints, toothpastes, tooth powders, prophylaxis pastes, lozenges, and gums.

The term "oral cavity" as referred to herein refers to the cavity from the lips to the epiglottis. The oral cavity comprises "hard tissues" comprising tissues such as the teeth and periodontal support and the like, as well as "soft tissues" which comprise tissues such as the gums, the tongue, the surfaces of the buccal cavity, and the like. Within the scope of this application, an "oral surface" includes the hard and soft tissues of the oral cavity.

In various embodiments, the orally acceptable vehicle used to prepare the oral care composition is aqueous. As recognized by one of skill in the art, the oral compositions of the present invention optionally include other materials, such as for example, anticaries agents, including the fluoride providing agents already described, desensitizing agents, viscosity modifiers, diluents, surface active agents, such as surfactants, emulsifiers, and foam modulators, pH modifying agents, abrasives, humectants, mouth-feel agents, sweetening agents, flavor agents, colorants, preservatives, and combinations thereof. It is understood that while general attributes of each of the above categories of materials may differ, there may be some common attributes and any given material may serve multiple purposes within two or more of such categories of materials. Preferably, the carrier materials are selected for compatibility with other ingredients of the composition.

Mouthrinses

The term "mouthrinse" in the present invention refers to oral compositions that are substantially liquid in character, such as a mouthwash, spray, or rinse. In such a preparation the orally acceptable vehicle is typically a water-and-alcohol mixture, desirably including a humectant and surfactant as described below. Generally, the weight ratio of water to alcohol is in the range of from about 1:1 to about 20:1, preferably about 3:1 to 10:1 and more preferably about 5:1 to about 8:1. The total amount of water-alcohol mixture in this type of preparation is typically in the range of from about 70% to about 99.9% by weight of the preparation. In various embodiments, the alcohol is typically ethanol or isopropanol.

The pH of such liquid and other preparations of the invention is generally in the range of from about 4.5 to about 9. The pH can be controlled with acid (e.g. citric acid or benzoic acid) or base (e.g. sodium hydroxide) or buffered (as with combinations of sodium citrate, benzoate, carbonate, or bicarbonate, disodium hydrogen phosphate, or sodium dihydrogen phosphate, for example).

An aqueous oral composition of the present invention such as a mouthrinse is prepared using an aqueous vehicle which preferably contains a humectant. The humectant may be a mixture of humectants, such as glycerin and sorbitol, and a polyhydric alcohol such as propylene glycol, butylene glycol, hexylene glycol, and polyethylene glycol. The humectant content is in the range of about 5% to about 40% by weight and preferably about 10% to about 30% by weight.

Surfactants useful in the present embodiment include anionic, nonionic, and zwitterionic surfactants. The surfactant is present in the aqueous oral compositions of the present invention range from about 0.1% to about 5% by weight, preferably from about 0.6% to about 2.0% by weight.

The mouthrinse and other liquid compositions (e.g. liquid dentifrice) may include at least one viscosity modifier, useful for example to inhibit settling or separation of ingredients or to promote redispersibility upon agitation of a liquid composition. Any orally acceptable viscosity modifier can be used, including without limitation mineral oil, petrolatum, clays and organomodified clays, silica and the like. One or more viscosity modifiers are optionally present in a total amount of about 0.01% to about 10%, for example about 0.1% to about 5% by weight of the composition.

Confectionery Compositions

The term "confectionery composition" as used herein includes within its meaning chewing gum, and orally soluble tablets, beads, lozenges, and films. Saliva dissolves the lozenge, film, or components of the chewable gum product and promotes prolonged contact with oral surfaces. Delivery of the water-soluble calcium salt and xylitol in a lozenge, tablet, bead, or chewing gum form ensures that an adequate dosage of the anti-caries ingredients are delivered to the oral surface when the product is used.

Lozenge/Bead/Tablet

The orally acceptable vehicle or carrier in a lozenge, bead, or tablet may be a non-cariogenic, solid, water-soluble, polyhydric alcohol (polyol), such as mannitol, xylitol, sorbitol, malitol, hydrogenated starch hydrozylate, hydrogenated glucose, hydrogenated disaccharides, or hydrogenated polysaccharides, preferably in an amount of about 85% to about 95% by weight of the total composition. Emulsifiers such as glycerin and tableting lubricants, in minor amounts of about 0.1% to 5% by weight, may be incorporated into the tablet, bead, or lozenge formulation to facilitate preparation. Suitable lubricants that may be incorporated as vegetable oils such as coconut oil, magnesium stearate, aluminum stearate, talc, starch, polyalkylene polyethers such as those under the name CARBOWAX (Dow Chemical, Midland, Mich., USA). Suitable non-cariogenic gums include kappa carrageenan, carboxymethyl cellulose, hydroxyethyl cellulose, and the like.

The lozenge, bead or tablet may optionally be coated with a coating material such as waxes, shellac, carboxymethyl cellulose, polyethylene/maleic anhydride copolymer or kappa carrageenan to further increase the time it takes the tablet or lozenge to dissolve in the mouth. An uncoated tablet or lozenge is slow-dissolving, providing a sustained release rate of active ingredients of about 3 to 5 minutes, depending upon the size of the lozenge.

Chewing Gum

The chewing gum of the present invention is preferably a sugarless chewing gum containing the xylitol and water-soluble calcium salt. Chewing gum formulations typically contain, in addition to a chewing gum base, one or more plasticizing agents, at least one sweetening agent, and at least one flavoring agent.

Suitable gum base materials suitable for use in the practice of this invention are well known in the art and include natural or synthetic gum bases or mixtures thereof. Representative natural gums or elastomers include chicle, natural rubber, jelutong, balata, guttapercha, lechi caspi, sorva, guttakay, crown gum, perillo, and mixtures thereof. Representative synthetic gums or elastomers include butadiene-styrene copolymers, polyisobutylene and isobutylene-isoprene copolymers. The gum base is incorporated in the chewing gum product at a concentration of about 10% to about 40% and preferably about 20% to about 35% by weight.

Plasticizing or softening agents commonly used in chewing gum compositions are suitable for use in this invention, including gelatin, waxes, and mixtures thereof in amounts of 0.1% to 5% by weight. A sweetening agent ingredient may be selected from a wide range of materials, and include the same artificial and polyol sweeteners used for the preparation of tablets, beads, and lozenges. Polyol sweeteners such as sorbitol and malitol are present in the chewing gum composition of the present invention in amounts of about 40% to about 80% by weight and preferably about 50% to about 75% by weight. The artificial sweetener is present in the chewing gum composition of the present invention in amounts of about 0.1% to about 2% by weight and preferably about 0.3% to 1% by weight.

Films

Films of the present invention may be in the form of an orally consumable film, which can include dissolvable films or films having a removable backing, as are known to those of skill in the art. Generally, such film compositions comprise a water soluble or dispersible film forming agent. Non-limiting examples may include water soluble polymers such as poly-vinyl pyrrolidone, hydroxyethyl cellulose, hydroxypropyl methyl cellulose, hydroxyalkyl celluloses, such as hydroxypropyl cellulose, carboxymethyl cellulose, polyvinyl alcohol, sodium alginate, alginate esters, guar gum, xanthan gum, gelatin, polyethylene oxide, polyethylene glycol, carrageenan, pullulan, locust bean gum as well as water dispersible polymers such as polyacrylates, carboxyvinyl copolymers, copolymers of methyl methacrylate, and polyacrylic acids. The film may also comprise hydrophobic film forming polymers, either as a removable backing layer, or mixed with a hydrophilic film forming polymer to alter dissolution rates of the film composition. In various embodiments, the film optionally comprises plasticizers, surface active agents, filler, bulking, or viscosity modifying agents, as well as flavor and sweetening components, as are well known in the art.

Dentifrices

In preferred embodiments of this invention, the oral composition may be a dentifrice. As referred to herein, a "dentifrice" is a composition that is intended for cleaning a hard surface within the oral cavity. Such dentifrices include toothpowder, a dental tablet, toothpaste (dental cream), or gel. In a toothpaste dentifrice, the orally acceptable vehicle may comprise water and humectant each typically in an amount ranging from about 10% to about 80% by weight of the oral composition.

Humectants

In various embodiments of the present invention, glycerin, propylene glycol, sorbitol, polypropylene glycol and/or polyethylene glycol (e.g., 400-600 average molecular weight) are suitable humectants/carriers. Also advantageous are liquid mixtures of water, glycerin, and sorbitol. In certain embodiments where the carrier is a clear gel and where the refractive index is an important consideration, the composition comprises about 3% to about 30% by weight of water, up to about 70% by weight of glycerin and about 20% to about 80% by weight of sorbitol.

Thickeners

In various embodiments, toothpastes, creams and gels contain a natural or synthetic thickener or gelling agent, which, other than silica thickeners, include natural and synthetic gums and colloids. In a still further embodiment a composition of the invention comprises at least one thickening agent, useful for example to impart a desired consistency and/or mouth feel to the composition. Any orally acceptable thickening agent can be used, including without limitation carbomers, also known as carboxyvinyl polymers, carrageenans, also known as Irish moss and more particularly ι-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. One or more thickening agents are optionally present in a total amount of about 0.01% to about 15%, for example about 0.1% to about 10% or about 0.2% to about 5% by weight of the composition.

Surface Active Agents

Various embodiments of the present invention also comprise a surface active agent, which may function as a surfactant, emulsifier, and/or foam modulator. Surface active agents generally achieve increased prophylactic action, by thoroughly dispersing the antibacterial system throughout the oral cavity. Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of about 0.01% to about 10%, for example about 0.05% to about 5% or about 0.1% to about 2% by weight of the composition.

Foam Modulators

Foam modulators useful herein include materials operable to increase amount, thickness, or stability of foam generated by the composition (e.g., dentifrice compositions) upon agitation. Any orally acceptable foam modulator can be used, including polyethylene glycols (PEGs), also known as polyoxyethylenes. High molecular weight PEGs are suitable, including those having an average molecular weight of about 200,000 to about 7,000,000, for example about 500,000 to about 5,000,000 or about 1,000,000 to about 2,500,000. one or more PEGs are optionally present in a total amount of about 0.1% to about 10% by weight, for example about 0.2% to about 5% by weight or about 0.25% to about 2% by weight.

Abrasives

In various embodiments of the present invention, where the vehicle of the oral care composition is solid or a paste, the oral composition preferably comprises a dentally acceptable abrasive material or polishing agent, which may serve to either polish the tooth enamel or provide a whitening effect. Any orally acceptable abrasive can be used, but type, fineness (particle size) and amount of abrasive should be selected so that tooth enamel is not excessively abraded in normal use of the composition. Suitable abrasives include without limitation silica, for example in the form of silica gel, hydrated silica or precipitated silica, alumina, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate. One or more abrasives are optionally present in an abrasive effective total amount, typically about 5% to about 70%, for example about 10% to about 50% or about 15% to about 30% by weight of the composition. Average particle size of an abrasive, if present, is generally about 0.1 to about 30 μm, for example about 1 to about 20 μm or about 5 to about 15 μm.

Water

In various embodiments of the present invention, water is also present in the oral composition, as referred to above. Water employed in the preparation of commercially suitable toothpastes, gels, and mouthwashes should preferably be deionized and free of organic impurities. The water is free water which is added, plus that which is introduced with other materials for example, such as that added with sorbitol. Water generally comprises from about 10% to 50%, preferably from about 20% to 40% by weight, of the toothpaste compositions herein. Water is a preferred diluent and in some compositions such as mouthwashes and whitening liquids is commonly accompanied by an alcohol, e.g., ethanol. The weight ratio of water to alcohol in a mouthwash composition is generally about 1:1 to about 20:1, for example about 3:1 to about 20:1 or about 4:1 to about 10:1.

Flavoring Agent

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methyl salicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include methol, menthyl acetate, menthyl lactate, camphor, eucalyptus oil, eucalyptol, anethole, eugenol, *cassia*, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of about 0.01% to about 5% by weight, optionally in various embodiments from about 0.05 to about 2% by weight, from about 0.1% to about 2.5% by weight, and from about 0.1 to about 0.5% by weight.

Sweeteners

Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from about 0.005% to about 5% by weight, optionally from about 0.01% to about 1% by weight.

Colorants

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001% to about 20% by weight, for example about 0.01% to about 10% by weight or about 0.1% to about 5% by weight.

Humectants

Humectants useful herein include polyhydric alcohols such as glycerin, sorbitol, xylitol and low molecular weight polyethylene glycols, including those listed above herein. In various embodiments, humectants are operable to prevent hardening of paste or gel compositions upon exposure to air. In various embodiments humectants also function as sweeteners. One or more humectants are optionally present in a total amount of about 1% to about 70% by weight, for example about 2% to about 25% by weight or about 5% to about 15% by weight.

pH Modifying Agents pH modifying agents among those useful herein include acidifying agents to lower pH, basifying agents to raise pH, and buffering agents to control pH within a desired range. For example, one or more compounds selected from acidifying, basifying, and buffering agents can be included to provide a pH of about 2 to about 10, or in various embodiments from about 2 to about 8, from about 3 to about 9, from about 4 to about 8, from about 5 to about 7, from about 6 to about 10, and from about 7 to about 9. Any orally acceptable pH modifying agent can be used including, but not limited to, those described above herein. One or more pH modifying agents are optionally present in a total amount effective to maintain the composition in an orally acceptable pH range.

Mouth-Feel Agents

Mouth-feel agents that may be used herein include materials which impart a desirable texture or other feeling during use of the composition. Such agents include bicarbonate salts, which in various embodiments impart a "clean feel" to teeth and gums due to effervescence and release of carbon dioxide. Any orally acceptable bicarbonate can be used, including without limitation alkali metal bicarbonates such as sodium and potassium bicarbonates, ammonium bicarbonate, and mixtures thereof. One or more bicarbonate salts are optionally present in a total amount of 0.1% to about 50%, for example about 1% to about 20% by weight.

Optional Active Materials

The compositions of the present invention optionally comprise one or more further active material(s), which is operable for the prevention or treatment of a condition or disorder of hard or soft tissue of the oral cavity, the prevention or treatment of a physiological disorder or condition, or to provide a cosmetic benefit. In various embodiments, the active is a "systemic active" which is operable to treat or prevent a disorder which, in whole or in part, is not a disorder of the oral cavity. In various embodiments, the active is an "oral care active" operable to treat or prevent a disorder or provide a cosmetic benefit within the oral cavity (e.g., to the teeth, gingiva or other hard or soft tissue of the oral cavity). Oral care actives among those useful herein include whitening agents, anticaries agents, tartar control agents, periodontal actives, abrasives, breath freshening agents, malodour control agents, tooth desensitizers, salivary stimulants, antibacterial agents, and combinations thereof. It is understood that while general attributes of each of the above categories of actives may differ, there may some common attributes and any given material may serve multiple purposes within two or more of such categories of actives.

Actives useful herein are optionally present in the compositions of the present invention in safe and effective amounts. A "safe and effective" amount of an active is an amount that is sufficient to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention. The specific safe and effective amount of the active will vary with such factors as the particular condition being treated, the physical condition of the subject, the nature of concurrent therapy (if any), the specific active used, the specific dosage form, the carrier employed, and the desired dosage regimen.

The compositions of the present invention optionally comprise a stannous ion source useful, for example, in helping reduce gingivitis, plaque, calculus, caries or sensitivity. One or more such sources can be present. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5% by weight of the composition.

The compositions of the present invention optionally comprise an antimicrobial (e.g., antibacterial) agent. One or more such agents can be present. Suitable examples include without limitation copper (II) compounds such as copper (II) chloride, fluoride, sulfate and hydroxide, zinc ion sources such as zinc acetate, zinc citrate, zinc gluconate, zinc glycinate, zinc oxide, zinc sulfate and sodium zinc citrate, phthalic acid and salts thereof such as magnesium monopotassium phthalate, hexetidine, octenidine, sanguinarine, benzalkonium chloride, domiphen bromide, alkylpyridinium chlorides such as cetylpyridinium chloride (CPC) (including combinations of CPC with zinc and/or enzymes), tetradecylpyridinium chloride and N-tetradecyl-4-ethylpyridinium chloride, iodine, sulfonamides, bisbiguanides such as alexidine, chlorhexidine and chlorhexidine digluconate, piperidino derivatives such as delmopinol and octapinol, magnolia extract, grapeseed extract, menthol, geraniol, citral, eucalyptol, antibiotics such as augmentin, amoxicillin, tetracycline, doxycycline, minocycline, metronidazole, neomycin, kanamycin and clindamycin, and the like. Other suitable antibacterial agents include non-ionic and anionic antibacterial agents known to one of skill in the art. Example non-ionic antibacterial agents include the substantially water insoluble, noncationic antibacterial agents such as alkylphenoxy phenols; cycloalkyl-phenoxyphenols; 9,10-dihydrophenanthrenol; alkylphenols; cycloalkyl-phenols; phenolic compounds; halogenated carbanilides; halogenated salicylanilides; benzoic esters; halogenated diphenyl ethers, and mixtures thereof. A particularly suitable non-ionic antibacterial agent is a diphenyl ether such as 2,4,4'-trichloro-2'-hydroxydiphenyl ether (Triclosan) and 2,2'-dihydroxy-5,5'-dibromodiphenyl ether. A further illustrative list of useful antibacterial agents is provided in U.S. Pat. No. 5,776,435 to Gaffar et al., issued Jul. 7, 1998 incorporated herein by reference. One or more antimicrobial agents are optionally present in an antimicrobial effective total amount, typically about 0.05% to about 10%, for example about 0.1% to about 3% by weight, of the composition.

The compositions of the present invention optionally comprise an antioxidant. Any orally acceptable antioxidant can be used, including butyrated hydroxyanisole (BHA), butyrated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention optionally comprise a sialogogue or saliva-stimulating agent, useful for example in amelioration of dry mouth. Any orally acceptable saliva stimulating agent can be used, including without limitation food acids such as citric, lactic, malic, succinic, ascorbic, adipic, fumaric, and tartaric acids, and mixtures thereof. One or more saliva stimulating agents are optionally present in a saliva stimulating effective total amount.

The compositions of the present invention optionally comprise an orally acceptable zinc ion source useful, for example, as an antimicrobial, anticalculus or breath-freshening agent. One or more such sources can be present. Suitable zinc ion sources include without limitation zinc acetate, zinc citrate, zinc gluconate, zinc glycinate, zinc oxide, zinc sulfate, sodium zinc citrate and the like. One or more zinc ion sources are optionally and illustratively present in a total amount of about 0.05% to about 3%, for example about 0.1% to about 1%, by weight of the composition.

The compositions of the present invention optionally comprise an antiplaque (e.g., plaque disrupting) agent. One or more such agents can be present in an antiplaque effective total amount. Suitable antiplaque agents include without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and chelating agents such as citric and tartaric acids and alkali metal salts thereof.

The compositions of the present invention optionally comprise an anti-inflammatory agent. One or more such agents can be present in an anti-inflammatory effective total amount. Suitable anti-inflammatory agents include without limitation steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone. One or more anti-inflammatory agents are optionally present in the composition in an anti-inflammatory effective amount.

The compositions of the present invention optionally comprise an $H_2$ histamine receptor antagonist. $H_2$ antagonists useful herein include cimetidine, etintidine, ranitidine, ICIA-5165, tiotidine, ORF-17578, lupititidine, donetidine, famotidine, roxatidine, pifatidine, lamtidine, BL-6548, BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, HB-408.4, and mixtures thereof.

The compositions of the present invention optionally comprise a desensitizing, or tooth sensitivity protecting, agent. One or more such agents can be present. Suitable desensitizing agents include without limitation potassium salts such as potassium citrate, potassium tartrate, potassium chloride, potassium sulfate and potassium nitrate. Another suitable desensitizing agent is sodium nitrate. Alternatively or in addition a local or systemic analgesic such as aspirin, codeine, acetaminophen, sodium salicylate or triethanolamine salicylate can be used. One or more desensitizing agents and/or analgesics are optionally present in a desensitizing and/or analgesic effective amount, typically about 0.05% to about 5%, for example about 0.1% to about 3% by weight, of the composition.

The compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), fish oil (including components thereof such as omega-3 (N-3) polyunsaturated fatty acids, eicosapentaenoic acid and docosahexaenoic acid), coenzyme Q10, and mixtures thereof.

The compositions of the present invention optionally comprise proteins. Suitable proteins include milk proteins and enzymes such as peroxide-producing enzymes, amylase, plaque-disrupting agents such as papain, glucoamylase, and glucose oxidase.

Methods

Methods are provided to treat or prevent dental caries in a human or animal subject comprising administering a safe and effective amount of an oral care composition to the oral cavity of the subject, the composition comprising: xylitol and a water-soluble calcium salt, wherein the xylitol and the calcium salt are present in a weight ratio of at least about 10:1. As used herein "animal subject" includes higher order non-human mammals such as canines and felines. The oral care composition is contacted with an oral surface of the mammalian subject to thereby provide xylitol and calcium and phosphate ions to promote remineralization and prevent demineralization of the teeth in a highly efficacious manner, without any negative interaction between the xylitol, the water-soluble calcium salt, and the orally acceptable vehicle.

In various embodiments, it is preferred that the oral care composition is applied and contacted with the oral surface. The dentifrice, confectionery, or mouthwash prepared in accordance with the present invention is preferably applied regularly to an oral surface, preferably on a daily basis, at least one time daily for multiple days, but alternately every second or third day. Preferably the oral composition is applied to the oral surfaces from 1 to 3 times daily, at a pH of about 4.5 to about 9, generally about 5.5 to about 8, preferably about 6 to 8, for at least 2 weeks up to 8 weeks, from two years to three years, or more up to lifetime.

Compositions of the present invention may also be used for the treatment or prevention of systemic disorders, such as the improvement of overall systemic health characterized by a reduction in risk of development of systemic diseases, such as cardiovascular disease, stroke, diabetes, severe respiratory infection, premature and low birth weight infants (including associated post-partum dysfunction in neurologic/developmental function), and associated increased risk of mortality. Such methods include those disclosed in U.S. Patent Publication 2003/0206874, Doyle et al., published Nov. 6, 2003, incorporated by reference.

The oral compositions of the present invention may be prepared by suitably mixing the ingredients. For instance, in the preparation of a mouthrinse, the xylitol and water-soluble calcium salt are dispersed in a mixture of ingredients, e.g., alcohol, humectants, surfactants, and flavor are then added and mixed. The ingredients are then mixed under vacuum for about 15-30 minutes. The resulting rinse product is then packaged. Dentifrices are prepared similarly, additional thickener and abrasives agents being included in the last step.

The invention is illustrated in the following examples.

EXAMPLES

Example 1

An oral care composition is prepared according to the following table. Xylitol is present in the composition at 10% by weight and prevents plaque formation and the development of *S. mutans*. Calcium glycerophosphate is present in the composition at 0.13% by weight and delivers calcium ions to the composition. Sodium monofluorophosphate is present in the composition at 1.10% by weight and delivers fluoride ions to the composition. The reduction in plaque formation and the delivery of calcium ions and fluoride ions to the teeth provides surprisingly high levels of remineralization in existing dental caries and also prevents new dental caries from developing.

| Ingredient | Weight Percent |
| --- | --- |
| Sorbitol 70% (w/w) | 30.0 |
| Xylitol | 10.0 |
| Deionized Water | 39.78 |
| Polyethylene Glycol 600 | 1.0 |
| Carboxymethyl Cellulose | 1.0 |
| Xanthan Gum | 0.3 |
| Sodium Saccharin | 0.2 |
| Sodium Monofluorophosphate | 1.10 |
| Calcium Glycerophosphate | 0.13 |
| Abrasive Silica (Zeodent 115) | 5.0 |
| Thickening Silica (Zeodent 165) | 8.0 |
| Titanium Dioxide | 0.5 |
| Sodium Lauryl Sulfate | 2.0 |
| Flavor Oil | 0.9 |
| Methyl Paraben | 0.075 |
| Propyl Paraben | 0.015 |
| Total Weight | 100.0 |

Example 2

The oral care composition according to Example 1 is administered to a German shepherd subject having carious lesions. The composition is spread on the oral and dental surfaces of the animal with an applicator once daily for two years to reduce the amount of *S. mutans* in the oral cavity and remineralize the teeth.

Example 3

The oral care composition according to Example 1 is administered to a human subject having no existing dental caries. The composition is applied with a toothbrush twice daily for three months to prevent dental caries and reduce plaque formation.

Example 4

An oral care composition is prepared according to the following table. The composition is administered to a subject as in Example 3.

| Ingredient | Weight Percent |
| --- | --- |
| Sorbitol 70% (w/w) | 53.0 |
| Xylitol | 10.0 |
| Deionized Water | 14.38 |
| Polyethylene Glycol 600 | 1.0 |
| Carboxymethyl Cellulose | 0.6 |
| Sodium Saccharin | 0.3 |
| Sodium Monofluorophosphate | 1.10 |
| Calcium Glycerophosphate | 0.13 |
| Abrasive Silica (Zeodent 115) | 8.0 |
| Thickening Silica (Zeodent 165) | 8.0 |
| Titanium Dioxide | 0.5 |
| Sodium Lauryl Sulfate | 2.0 |

-continued

| Ingredient | Weight Percent |
| --- | --- |
| Flavor Oil | 0.9 |
| Methyl Paraben | 0.075 |
| Propyl Paraben | 0.015 |
| Total Weight | 100.0 |

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

What is claimed is:

1. An oral care composition comprising:
   xylitol,
   sorbitol,
   a water-soluble calcium salt comprising calcium glycerophosphate, and
   a fluoride-providing agent;
   wherein said xylitol and said calcium salt are present in a weight ratio of about 65:1 to about 80:1,
   said sorbitol is present in an amount from about 30% to about 80% by weight,
   said xylitol is present in an amount from about 5% to about 20%, and
   said water-soluble calcium salt is present in an amount from about 0.01% to about 1% by weight.

2. An oral care composition according to claim 1, wherein said water-soluble calcium salt further comprises at least one member from the group consisting of calcium chloride, calcium acetate, calcium butyrate, calcium citrate, calcium lactate, calcium salicylate and mixtures thereof.

3. An oral care composition according to claim 1, wherein said calcium glycerophosphate is selected from the group consisting of: α-calcium glycerophosphate, β-calcium glycerophosphate, and mixtures thereof.

4. An oral care composition according to claim 1, comprising from about 8% to about 15% by weight xylitol.

5. An oral care composition according to claim 4, comprising from about 0.08% to about 0.3% by weight of said water-soluble calcium salt.

6. An oral care composition according to claim 5, wherein said fluoride-providing agent is sodium monofluorophosphate.

7. An oral care composition according to claim 5, wherein said fluoride-providing agent is present in an amount sufficient to provide from about 200 ppm to about 3000 ppm fluoride ion.

8. An oral care composition according to claim 5, wherein said fluoride-providing agent is present in said composition from about 0.001% to about 3% by weight.

9. An oral care composition according to claim 1, wherein said oral care composition is selected from the group consisting of: mouth rinses, mouthwashes, liquid dentifrices, dental films, dental strips, paint on gels, dental beads, confectionaries, lozenges, gums, toothpastes, dental gels, dental creams, and toothpowders.

10. An oral care composition according to claim 1, further comprising at least one of a surfactant, a humectant, a sweetener, a thickener, an abrasive, a flavorant, and a preservative.

11. An oral care composition according to claim 10, comprising a preservative selected from the group consisting of:

parabens, dehydroacetic acid, sorbic acid, sodium benzoate, potassium sorbate, and mixtures thereof.

12. An oral care composition comprising
an anti-cariogenic amount of xylitol,
sorbitol in an amount from about 30% to about 80% by weight,
an anticariogenic amount of calcium glycerophosphate and
an anti-cariogenic amount of a fluoride providing agent,
wherein said xylitol and said calcium glycerophosphate are present in a weight ratio of at least about 10:1.

13. An oral care composition according to claim 1, wherein said
said xylitol and said calcium salt are present in a weight ratio of 65:1 to 80:1,
said sorbitol is present in an amount from 30% to 80% by weight,
said xylitol is present in an amount from 5% to 20%, and
said water-soluble calcium salt is present in an amount from 0.01% to 1% by weight.

* * * * *